United States Patent
Richman

(10) Patent No.: US 6,455,854 B1
(45) Date of Patent: Sep. 24, 2002

(54) INFRARED RADIATION DETECTOR FOR MONITORING THE PRESENCE OF ALKANES

(75) Inventor: Lee Richman, Poole (GB)

(73) Assignee: Zellweger Analytics Limited, Poole (GB)

( * ) Notice: Subject to any disclaimer, the term of this patent is extended or adjusted under 35 U.S.C. 154(b) by 0 days.

(21) Appl. No.: 09/529,090

(22) PCT Filed: Oct. 6, 1998

(86) PCT No.: PCT/GB98/02991

§ 371 (c)(1), (2), (4) Date: Jul. 24, 2000

(87) PCT Pub. No.: WO99/19712

PCT Pub. Date: Apr. 22, 1999

(30) Foreign Application Priority Data

Oct. 10, 1997 (GB) ............................................. 9721608
Oct. 10, 1997 (GB) ............................................. 9721609

(51) Int. Cl.[7] .................................................. G01J 5/02
(52) U.S. Cl. .................................. 250/343; 250/339.01
(58) Field of Search .......................... 250/343, 339.01, 250/336.1, 345, 340, 341, 373; 356/437, 411, 409

(56) References Cited

U.S. PATENT DOCUMENTS 6,061,141 A    5/2000  Goldenberg et al. ........ 356/437

FOREIGN PATENT DOCUMENTS

| EP | 744615 | 11/1995 |
|----|--------|---------|
| GB | 1402301 | 8/1975 |
| GB | 1402302 | 8/1975 |
| GB | 2008745 | * 6/1979 |
| GB | 2163251 | 2/1986 |

* cited by examiner

Primary Examiner—Hung Xuan Dang
(74) Attorney, Agent, or Firm—Andrus, Sceales, Starke & Sawall, LLP

(57) ABSTRACT

The present invention relates to the infrared detection of hydrocarbon gases; infrared light from a source (10) is passed through a filter (12) to produce a beam (14) passing through a space (16), which can potentially contain hydrocarbon gases. The wavelength of the beam (14) contains a wavelength that is absorbed by hydrocarbon gases (sample wavelength) and a wavelength that is not absorbed by hydrocarbon gases (reference wavelength). The beam (14) falls on a detector that contains sensors (22, 24) that receive light that has passed through respective filters (18, 20). Sample filter (20) allows a single wavelength to be transmitted; reference filter (18) allows two wavelength bands to be transmitted, the bands having wavelengths located on either side of the sample wavelength in order to eliminate the effects of atmospheric conditions that are unconnected with hydrocarbon gases.

12 Claims, 2 Drawing Sheets

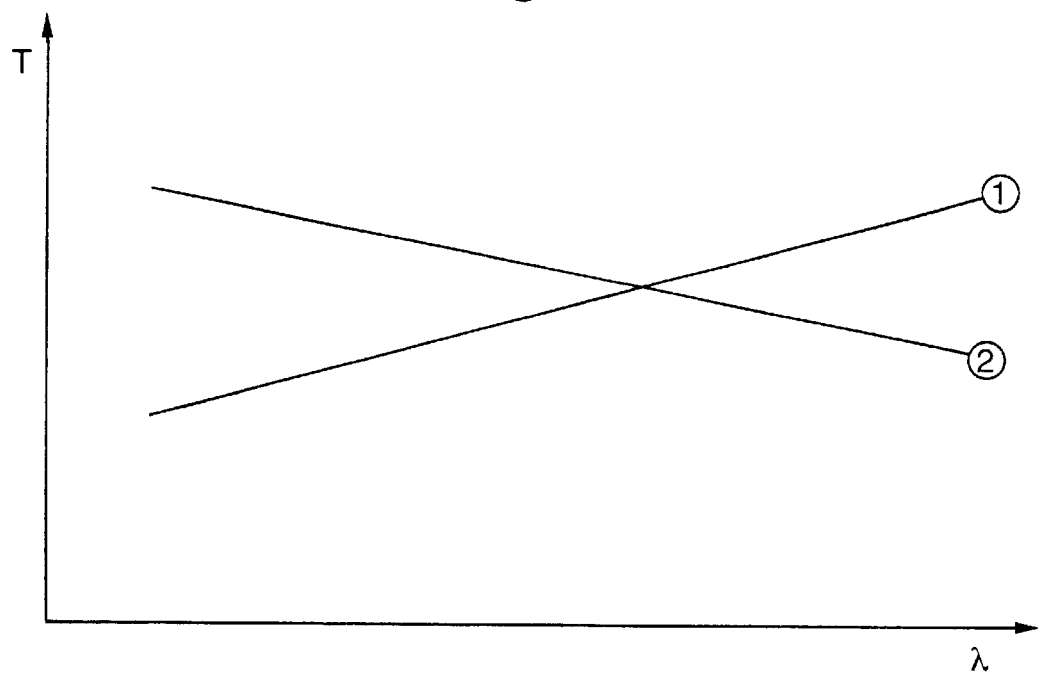
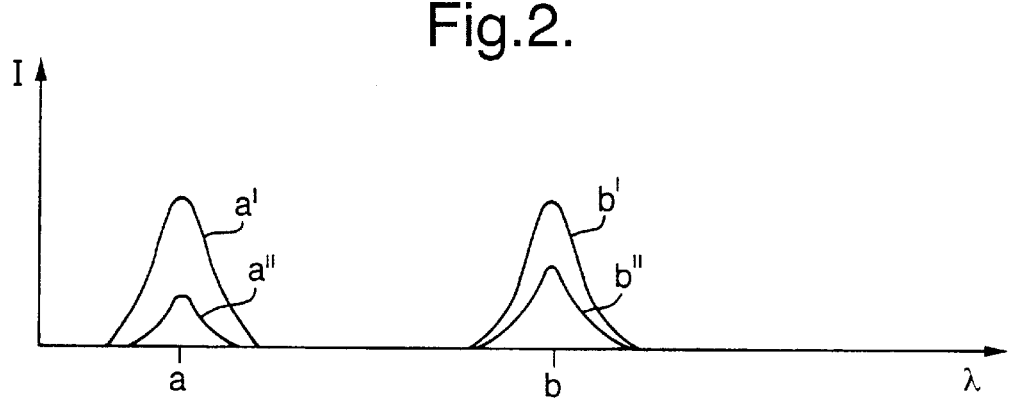
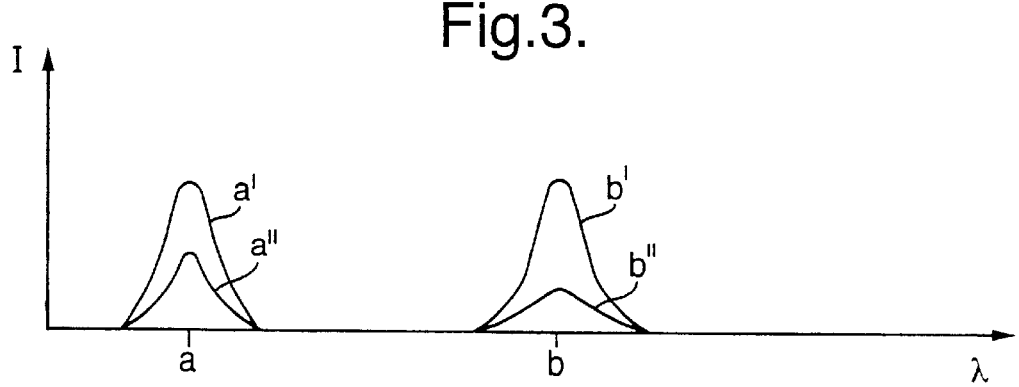

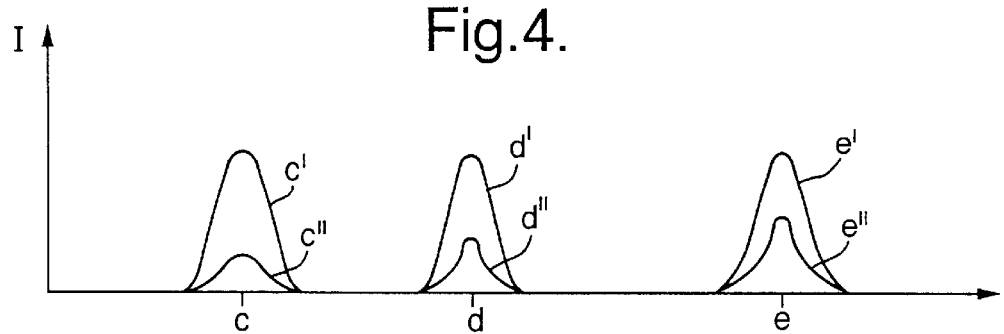
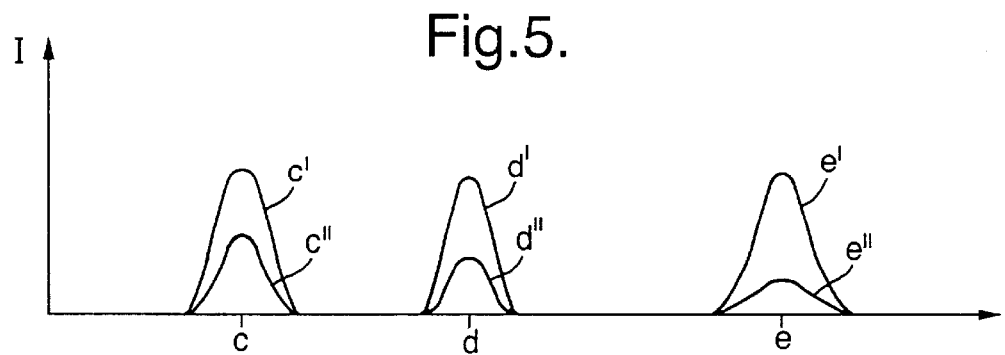
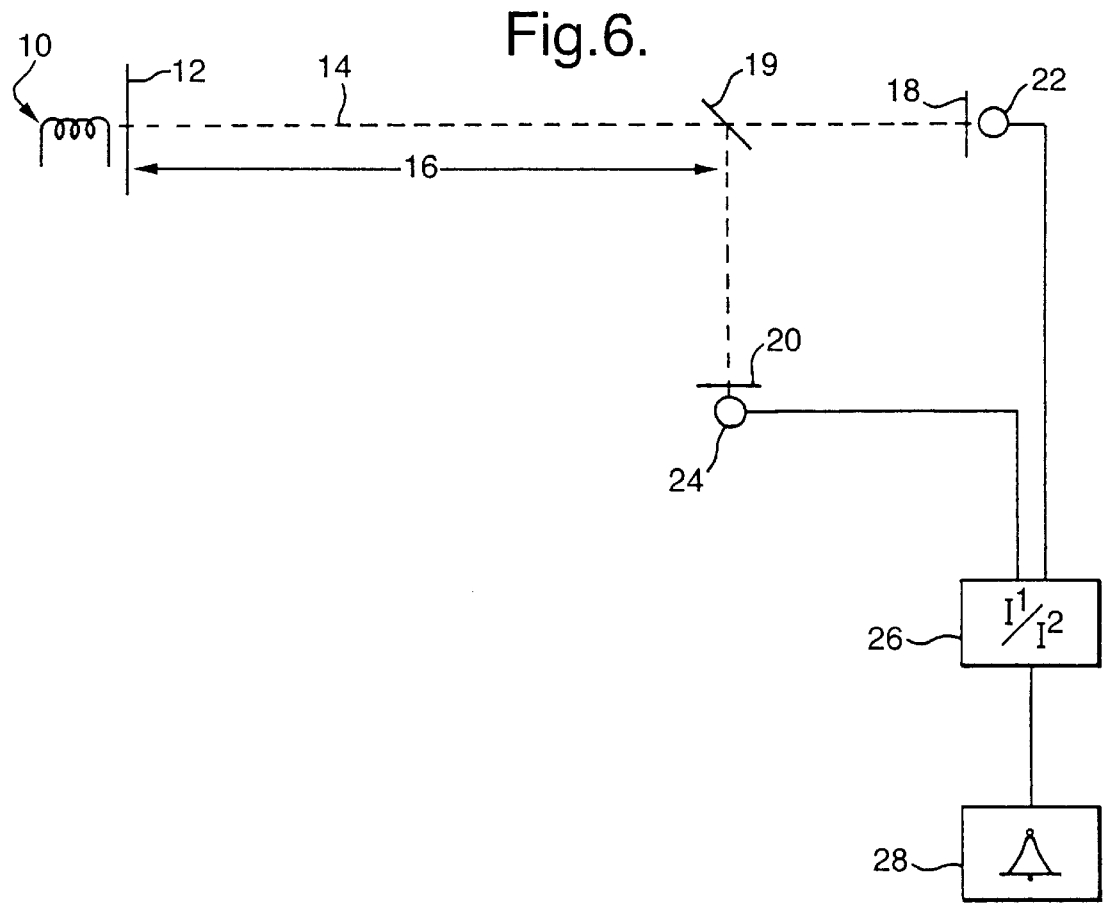

INFRARED RADIATION DETECTOR FOR MONITORING THE PRESENCE OF ALKANES

INDUSTRIAL FIELD

The present invention relates to the infrared detection of hydrocarbon gases (which term includes vapours).

BACKGROUND ART

The use of non-dispersive infrared spectroscopy to detect gases is well established. It essentially involves transmitting infrared radiation along a path in an area being monitored; the wavelength of the infrared radiation is chosen so that it is absorbed by the gas of interest (hereafter called the "target gas") but not substantially absorbed by other gases in the atmosphere of the area being monitored. If monitoring out-of-doors, the wavelength should ideally not be absorbed by liquid water (e.g. in the form of condensation, rain or spray). The intensity of the radiation that has passed along the path in the area being monitored is measured and the attenuation in the intensity of the radiation gives a measure of the amount of the target gas in the monitored area.

However, factors other than absorption by the target gas also attenuate the infrared radiation including obscuration of the detecting beam, atmospheric scattering of the radiation, contamination of optical surfaces, e.g. by dirt or condensation, and ageing of components. The reliability of infrared gas detectors is significantly improved by the use of a reference; such a reference is usually infrared radiation at a different wavelength, which ideally is a wavelength at which the target gas does not exhibit significant absorption. The ratio between the signal obtained at the wavelength where the target gas does absorb (the "sample wavelength") and the signal obtained at the wavelength where the target gas does not significantly absorb (the "reference wavelength") compensates for the attenuation caused by non-target gases since ideally the signal at the reference wavelength and the signal at the sample wavelength will both be affected by such non-target gas attenuation.

A known infrared detector is a so-called "fixed point" detector, which has a very short path length (e.g. up to 10 cm) and so only monitors a relatively small space. It can be used to detect leakages of hydrocarbons from oilrigs, pipelines, storage tanks or refineries. The provision of such detectors in open spaces away from a leakage site may result in the leakage not being detected since prevailing atmospheric conditions (e.g. wind speed, wind direction and temperature) could carry the gas away from the detectors, which would then not register the leakage. It is therefore a difficult task to position such fixed point detectors and usually a compromise is drawn in the location of detectors, based on likely leak sites and typical prevailing weather conditions; also the number of such detectors that can be provided is limited by cost. Generally fixed-point detectors are used for monitoring of specific items of equipment and apparatus that are liable to leak, for example pipeline joints and valves.

Fixed-point detectors are coupled with an alarm that indicates the detection of a target gas in the immediate neighbourhood of the detector. Because such detectors are placed near the source of any leak, any significant leaking target gas will be in relatively high concentration in and around the detector. It is therefore possible to set the alarm such that the amount of the target gas present before the alarm is triggered is relatively large, thereby avoiding the giving of false alarms. The giving of false alarms is a substantial problem since it could result in the shutting down of a facility, for example an oil rig or an oil refinery.

To overcome the above-mentioned shortcomings of fixed-point detectors, longer path-length gas detectors, so called "open-path optical gas detectors", are used, in which radiation at sample and reference wavelengths is transmitted along an open-path which passes through the atmosphere in the space to be monitored. The length of the path can vary from one to a thousand meters, depending on the application, and so allows a much greater space to be monitored than is the case with fixed-point detectors. When used out-of-doors, the open nature of the optical path means that the beam is exposed to prevailing atmospheric weather conditions, which can seriously affect the operation of the instrument. For example, rain, snow, mist, fog, sea spray, blizzards and sand or dust storms scatter or absorb radiation at the reference and sample wavelengths. The level of absorption and scattering by such weather conditions depends on the size, shape, nature and optical properties of the droplets, drops or particles concerned. Unfortunately such attenuation is not uniform across the infrared spectrum, i.e. the attenuation at the sample wavelength and the attenuation at the reference wavelength are not identical which gives rise to errors in the measurement of the amount of target gas and can, in extreme cases, lead to the failure to trigger an alarm or the triggering of a false alarm. The matter is complicated considerably because different weather conditions exhibit different relative and absolute attenuation at the sample and reference wavelengths. For example, one sort of fog can attenuate the radiation at the reference wavelength more than the radiation at the sample wavelength whereas a different sort of fog will attenuate the radiation at the sample wavelength more than the radiation at the reference wavelength. The variability of atmospheric attenuation for different weather conditions makes it very difficult to compensate for the effects of weather upon this sort of gas detector.

In order to minimise the differential attenuation between the sample wavelength and the reference wavelength, it is preferable that the two wavelengths are as close as possible to each other. However, this is not always possible since there may not be a suitable reference wavelength, i.e. a wavelength at which the target gas is only minimally absorbed, near the sample wavelength. The situation is made even more complex because of the need to avoid cross-sensitivity to other atmospheric gases, the absorption/refraction characteristics of water droplets that may be present in the path of the infrared beam and the band shapes and tolerances of the filters used to restrict the sample and reference wavelengths. Thus there may be several hundred nanometers between the sample and reference wavelengths. This separation can result in significant differences between the absorption characteristics of the sample and reference wavelengths under different weather conditions, as set out above.

Instead of measuring the reference signal at a single wavelength, it has been proposed (see for example GB-1,402,301, GB-1,402,302, U.S. Pat. No. 4,567,366, EP-0,744,615 and GB-2,163,251) to use two reference wavelengths located on either side of a sample wavelength and take, as the reference signal, the average of the signals at the two reference wavelengths. This arrangement requires the measurement of light absorption at two different reference wavelengths, which in turn requires either the use of separate light beams to measure the absorption at each of the two reference wavelengths or the use of a mechanical arrangement to bring two filters into alignment with a single light-sensitive detector. Both solutions will work satisfactorily in a laboratory but not in the field, particularly not in the harsh environments encountered on offshore oil/gas platforms or in the Middle East, the Tropics, the Arctic, etc. The use of two reference light beams (in addition to the sample light beam) requires careful alignment (within micron tolerances) of the detectors and it is difficult enough to align the detectors for the sample beam and a single reference beam, let along aligning an additional detector for a second reference beam. Furthermore, the buffeting of the detectors in the environment of the North Sea, for example, can displace the alignment. In addition, the use of an additional reference beam makes the system expensive. The use of a mechanical arrangement (e.g. a spinning filter wheel) to bring sample and reference filters periodically into alignment with a single light-sensitive detector is also not feasible in the field since vibrations can affect the operation of the mechanical arrangement and such mechanical parts can be unreliable in the harsh environmental conditions encountered.

It is also known to use as the reference a broad range of wavelengths, and if the range includes the sample wavelength, it is possible to make the average reference wavelength equal to the sample wavelength, thereby eliminating the problems discussed above of having the reference and sample wavelengths distant from each other. However, the inclusion in the reference signal of a substantial component made up of the sample signal itself leads to substantially reduced sensitivity.

All the $C_{1-7}$ alkanes are gaseous or volatile and their escape can give rise to a risk of an explosion and therefore it is necessary to monitor for the presence of any of them. It is not feasible to provide separate systems for detecting each alkane and therefore it is necessary that a single system should be capable of detecting all these alkanes. However, the alkanes all have different spectra and so it is difficult to select a single sample wavelength and a single reference wavelength that can be used for all of the $C_{1-7}$ alkanes.

A further substantial problem underlying the use of this type of detector is the need to avoid false alarms being given, which can result in the shut down of a complete facility, for example oil pipeline, oil refinery or oil rig. It is obviously desirable to be able to detect the smallest possible concentration of the target gas that could give rise to a hazard. However, this must be set against the need to avoid false alarms and the above-described problem of atmospheric conditions differentially affecting the reference and sample wavelengths.

It is an object of the present invention to provide an infrared detector of the open path type described that is capable of monitoring for all, of the $C_{1-7}$ alkanes and yet is sufficiently rugged that it can be operated reliably in the field in harsh environments. It is a further object of the present invention to provide an infrared detector that will have an improved accuracy for detecting alkanes in a variety of harsh weather conditions as compared to known open path infrared detectors so that the instances of false alarms are reduced.

DISCLOSURE OF THE INVENTION

According to the present invention there is provided an infrared gas detector for a target gas comprising:

an infrared source capable of transmitting at least one infrared beam comprising radiation in at least one wavelength band at which the target gas is absorbent (sample wavelength band) and in at least one wavelength band at which the target gas is only absorbent to a substantially lesser extent than at the sample wavelength band (reference wavelength band);

a first radiation intensity sensor capable of sensing the intensity of the infrared radiation in the sample wavelength band(s) and a second radiation intensity sensor capable of sensing the intensity of the infrared radiation in the reference wavelength band(s), both of which are spaced apart from the transmitter by a beam path; and a first filter that is located in front of the first sensor and that only transmits one or more sample wavelength bands and a second filter that is located in front of the second sensor and that only transmits one or more reference wavelength bands, wherein the aggregate number of sample and reference wavelength bands transmitted by the two filters is at least three and wherein the centre of the sample wavelength band (if there is only one sample wavelength band) or the mid point between the sample wavelength bands (if there are multiple sample wavelength bands) is approximately the same as the centre of the reference wavelength band (if there is only one reference wavelength band) or the mid point between reference wavelength bands (if there are multiple reference wavelength bands).

By making the mid-point of the reference wavelenlgth band(s) approximately the same as the mid-point of the sample wavelength band(s), the differential attenuation of radiation at the sample and reference wavelengths caused by atmospheric conditions can be eliminated or substantially reduced. As indicated, the aggregate number of sample and reference wavelength bands transmitted by the two filters can exceed three so long as the mid point between the bands at the sample wavelengths is approximately the same as the mid point of the bands at the reference wavelengths, although exact coincidence of the two mid points is not required.

A single infrared beam emitted by the transmitter can contain the sample and the reference wavelength bands or separate beams may be provided. Indeed, the beam emitted by the transmitter can include a wide spectrum of wavelengths, not only the sample and reference wavelength bands. A filter may be inserted in the infrared beam in order to transmit along the detection path only wavelengths around the wavelengths detected by the detector sensor(s) but such a filter is not necessary. The use of two separate radiation intensity sensors, one for the sample wavelength band(s) and the other for the reference wavelength band(s) means that there are only two sensors in the system that need aligning and there is no need to move the first and second filters.

In order to discriminate between infrared radiation from the transmitter and infrared radiation from other potentially interfering sources of radiation, e.g. sunlight, the radiation from the transmitter is preferably modulated with a distinct characteristic that can be recognised by the receiver; this modulation can be achieved in many ways, including pulse or amplitude modulation of the infrared source's drive voltage/current, acousto-optic modulation and electro-optic modulation. In the preferred embodiment, the modulation is achieved by pulsing the voltage applied to a flashlamp, e.g. a Xenon arc flashlamp. This pulsing produces short, very high intensity pulses that are easily discriminated from both natural and artificial sources that are likely to be encountered in the intended operating environment.

One highly important aspect of the present invention is the selection of the sample and reference wavelength bands that allow the reliable detection of $C_{1-7}$ alkanes. The first (sample) filter advantageously transmits a single band having a central wavelength of 2300±5 nm and a full width half maximum (FWHM) of 50±10 nm. The second (reference) filter is preferably a dual bandpass filter having a first band centred around 2215±5 nm with a FWHM of 25±5 nm and a second band having a central wavelength of 2385±5 nm and a FWHM of 25±5 nm. It can be seen that the sample wavelength band lies mid way between the two reference wavelength bands of the dual bandpass reference filter. The selection of these wavelengths is not apparent from the spectra of $C_{1-7}$ alkanes since some of the alkanes are significantly absorbent at the reference wavelengths and yet, as shown below, we have surprisingly shown that the choice of these wavelengths provides good detection of $C_{1-7}$ alkanes and avoids giving false alarms even in the presence of rain and fog.

DETAILED DESCRIPTION OF DRAWINGS

The present invention will be further described by way of example only with reference to the following drawings in which:

FIG. 1 is a schematic graph showing the change in the transmission characteristics of the beam path without any target gas being present as a function of wavelength in the presence of two different types of atmospheric conditions 1 and 2;

FIG. 2 is a schematic graph of the intensity of infrared radiation in the sample and reference bands in the prior art arrangement without any target gas being present, as modified by environmental condition 1 of FIG. 1;

FIG. 3 is a schematic graph of the intensity of infrared radiation in the sample and reference bands in the prior art arrangement without any target gas being present, as modified by environmental condition 2 of FIG. 1;

FIG. 4 is a schematic graph of the intensity of infrared radiation in the sample and reference bands according to the present invention without any target gas being present, as modified by environmental condition 1 of FIG. 1;

FIG. 5 is a schematic graph of the intensity of infrared radiation in the sample and reference bands according to the present invention without any target gas being present, as modified by environmental condition 2 of FIG. 1; and FIG. 6 is a schematic view of the detector of the type used in the present invention and in the prior art. The difference between the present invention and the prior art lies in the nature of the filters, as explained in further detail below.

DETAILED DISCLOSURE OF PREFERRED EMBODIMENTS

Referring initially to FIG. 6, there is shown a source of infrared radiation, which in the present invention is preferably a flash lamp 10, placed behind a filter 12 that transmits infrared radiation in sample and reference wavelength bands, as described in further detail below. The beam 14 transmitted by filter 12 passes along beam path 16, which can vary in length from one to a thousand meters, and is attenuated by material in that path. The beam 14 attenuated in this way is incident on a receiver 17 containing a beam splitter 19; filters 18 and 20 and corresponding intensity measuring sensors 22 and 24 are placed in the two parts of the split beams. Filter 18 transmits radiation only at the sample wavelengths and filter 20 transmits radiation only at the reference wavelengths.

In prior art arrangements, filter 20 transmits in a single sample wavelength band and the filter 20 transmits in a single reference wavelength band as described below with reference to FIGS. 2 and 3. In the exemplified detector of the present invention filter 18 is a single bandpass filter transmitting radiation in one distinct source infrared band and filter 20 is a dual bandpass filter transmitting radiation in two distinct reference infrared bands that lie either side of the sample band of filter 18, as described below with reference to FIGS. 4 and 5.

The signals from sensors 22 and 24 are fed into a circuit 26 that can calculate the ratio between these two signals. If there is target gas in the path of the beam 14, radiation in the sample wavelength band is absorbed by the target gas whereas radiation in the reference wavelength band is not (or at least not to the same extent). The ratio of the intensity of the signal of sensor 22 (measuring the sample wavelengths) as compared to the signal of sensor 24 (measuring the reference wavelengths) will therefore fall in the presence of a target gas and if the ratio falls below a threshold value, an alarm 28 is triggered indicating the presence of the target gas. The threshold value can be set by the user.

Referring to FIG. 1, which shows the transmittance (T) of the signal from the radiation source 10 and filter 12, as attenuated by environmental conditions 1 and 2 prevailing along beam path 16. As can be seen, under environmental condition 1, the transmittance of the beam is greater at higher wavelengths than at lower wavelengths whereas the situation is completely the other way round under environmental conditions 2; as mentioned above, fog can constitute both environmental condition 1 and environmental condition 2, depending on the size of the water droplets in the fog. Referring to FIG. 2, there is shown a plot of radiation intensity against wavelength; in the known prior art open path infrared gas detectors, a single sample wavelength band A and a single reference wavelength band B are used. The intensity of radiation in the sample wavelength band A incident on sensor 22 and the intensity of radiation in the reference wavelength band B incident on sensor 24 are shown. The upper curves, a' and b', show the intensities that are unattenuated by environmental conditions 1 or 2. However, the lower curves, a" and b" show the resulting curves when environmental condition 1 is prevailing. As can be seen from FIG. 2, under environmental conditions 1, the reference intensity (band B) is greater than the sample intensity (band A) even though there is no target gas in the beam path; such a relationship between the two signals is the usual indicator that there is some target gas in the space being monitored. Thus, environmental conditions 1 can lead to a premature triggering of the alarm 28 indicating the presence of a hydrocarbon when, in fact, that is not the case.

Referring now to FIG. 3, it can be seen that the attenuation of the sample and reference signals under environmental conditions 2 mean that the sample intensity a" is greater than the reference intensity b". Therefore, the presence of a greater amount of hydrocarbon gas is required in order to trigger off the alarm signal under environmental conditions 2 than would normally be the case.

Referring to FIG. 4, the corresponding conditions are shown using the detector according to the present invention. In this embodiment, a single sample wavelength band D is used, which is situated between (and preferably mid-way between) two reference wavelength bands C and E. Under environmental condition 1. the intensity of the radiation c" in reference band C is smaller than the intensity d" at sample wavelength band D which in turn is smaller than the intensity e" at reference wavelength band E. However, since the signal produced by intensity sensor 24 results from the combined intensities c" and e" of reference bands C and E, the "average" attenuation on the two reference bands C and E under environmental condition 1 is approximately the same as the attenuation of wavelength band D, i.e. the differential attenuation at different wavelengths is cancelled out and so the ratio of the signal at sensor 22 resulting from sample wavelength band D to the signal at sensor 24 resulting from the combined intensities at wavelength bands C and E properly reflects the amount of target gas in the beam path.

Referring to FIG. 5, there is shown the corresponding position resulting from environmental condition 2. Again, the ratio of the signal at sensor 22 resulting from sample wavelength band D to the signal at sensor 24 resulting from the combined intensities at wavelength bands C and E properly reflects the amount of target gas in the beam path and is more or less the same as that prevailing in environmental condition 1.

The above system is predicated on the assumption that the attenuation brought about by different environmental conditions is linear across the infrared spectrum. Whereas this is rarely, if ever, the case, we have found that the attenuation brought about by environmental conditions can generally be approximated to linear. Whether the attenuation is exactly linear or not, it can be seen that, by comparing the bands in FIGS. 4 and 5 with those of FIGS. 2 and 3, the present invention provides a significant benefit over the prior art.

The selection of the sample and the reference wavelength bands will depend on the nature of the target gas and the nature of other gases in the space being monitored and can be selected by an analysis of the infrared spectra of the gases involved, preferably also taking into account the spectrum of liquid water. They should be chosen such that the mid-point of the sample wavelengths and the mid-point of the reference wavelengths are as close to each other as possible.

EXAMPLE

We have found that the reference filter 20 for the detection of $C_{1-7}$ alkane hydrocarbon gases, while avoiding the effects of water, is preferably a dual bandpass filter having a first band centred around 2215±nm (preferably 2215±10 nm and more preferably 2215±5 nm) with full width half maximum (FWHM) of 25±20 nm (preferably 25±10 nm and more preferably 25±5 nm). The second band of filter 20 has a central wavelength of 2385±20 nm (preferably 2385±10 nm and more preferably 2385±5 nm) and a FWHM of 25±20 nm (preferably 25±10 nm and more preferably 25±5 nm).

The sample filter 18 transmits a single band having a central wavelength of 2300±20 nm (preferably 2300±10 nm and more preferably 2300±5 nm) and a FWHM of 50±20 nm (preferably 50±10 nm). Thus it can be seen that the sample wavelength band lies mid way between the reference wavelength bands of dual bandpass filter 20.

In order to demonstrate the effect of the present invention, two open path gas detectors were used. One was a conventional Searchline Excel open path gas detector obtainable from Zellweger Analytics (Hatch Pond House, 4 Stinsford Road, Nuffield Estate, Poole, Dorset BH1 0RZ, United Kingdom) fitted with conventional, single bandpass sample and reference filters, the other was an identical Searchline Excel detector but modified by using different sample and reference filters so that the detector was in accordance with the present invention. The filters used were narrow bandpass sample filter and a double bandpass reference filter. The centre wavelengths and the full width half maximum values of the filters of the two detectors are set out in Table 1.

TABLE 1

| | Centre Wavelength(s) | FWHM |
|---|---|---|
| Conventional Detector | | |
| Sample | 2,300 nm ± 25 nm | 200 nm ± 25 nm |
| Reference | 2,100 nm ± 25 nm | 200 nm ± 25 nm |
| Detector according to the Present Invention | | |
| Sample (Narrowband): | 2,300 nm ± 5 nm | 50 nm ± 5 nm |
| Reference (Double bandpass) | 2,215 nm ± 5 nm | 25 nm ± 5 nm |
| | & | & |
| | 2,385 nm ± 5 nm | 25 nm ± 5 nm |

The two gas detectors were tested by aligning each detector such that their beams passed through a tunnel in which controlled, simulated fog conditions could be produced. The detectors were then zeroed and calibrated using a standard procedure.

Whilst monitoring the gas reading (measured in lower explosive limit (LEL).m) from the detectors under test, the density of fog in the tunnel was gradually increased from zero up to an attenuation of 2,000:1. At regular intervals, the detectors were functionally tested using plastic test filters, which simulate a nominal 3.0 LEL.m gas cloud.

It was found that the detector fitted with the conventional filters showed a steady increase in gas reading as the fog density increased. This reading reached 0.5 LEL.m at an attenuation of 40:1. The detector continued to function up to 2,000:1 attenuation but with a significantly offset zero.

The detector unit fitted with the filters of the present invention showed no significant gas reading as the fog density was increased. The detector continued to function acceptably up to 2.000:1 attenuation. The only change in behaviour noticed at high attenuations was a slight increase in response to the plastic functional test filter.

The detector unit fitted with conventional filters exhibited a significant response to fog. The first alarm threshold for most applications in which open path gas detectors are used is generally set at 1.0 LEL.m. In order to ensure that false alarms are not generated by environmental conditions, a maximum zero offset of 0.5 LEL.m is allowable. The detector fitted with conventional filters exceeded this for fog attenuations of 40:1 (approximately 25 meters visibility). This imposes a restriction on the density of fog in which the detector can be allowed to remain operational.

The detector fitted with the new design of filters exhibited no significant response to fog up to attenuations of 2,000:1. The slight increase in test filter response was not significant and was in the safe direction (i.e. increased the output). The performance enhancement achieved with the use of the new filters enables high integrity operation in fog conditions with attenuation up to at least 500:1. This is sufficient to enable operation in all but the most extreme fog conditions, which are rare enough to represent no significant operational problem.

What is claimed is:

1. An infrared gas detector, said detector monitoring for the presence of one or more of a plurality of target gases comprising volatile, potentially explosive $C_{1-7}$ alkane compounds having differing infrared absorption spectra, said detector accurately indicating the concentration of such gases in service environments exhibiting differential attenuation of infrared radiation; said detector comprising:

an infrared radiation source for transmitting at least one beam of infrared radiation having a wavelength range that includes wavelengths of substantially 2215, 2300, and 2385 nm;

a first filter spaced from said radiation source along a beam path in which the one or more target gases are received and which is subjected to the service environment of the detector, said first filter receiving radiation from the beam traversing the beam path, said first filter transmitting radiation in a band having a central wavelength of 2300±20 nm and a full width half maximum of 50±20 nm to form a first wavelength band for said detector;

a dual bandpass, second filter spaced from said radiation source along said beam path, said second filter receiving radiation from the beam and transmitting radiation in a band having a central wavelength of 2215±20 nm and a full width half maximum of 25±20 nm to form a second wavelength band for said detector, said second filter further transmitting radiation in a band having a central wavelength of 2385±20 nm and a full width half maximum of 25±20 nm to form a third wavelength band for said detector;

a first radiation sensor for sensing the intensity of radiation in said first wavelength band;

a second radiation sensor for sensing the intensity of radiation in said second and third wavelength bands; and means responsive to said first and second radiation sensors for indicating the presence of one or more target gases.

2. An infrared gas detector as claimed in claim 1, wherein said first filter transmits a first wavelength band having a central wavelength of 2300 ±5 nm and said dual band pass second filter transmits second and third wavelength bands having central wavelengths of 2215±5 nm and 2385±5 nm, respectively.

3. An infrared gas detector as claim in claim 1, wherein the infrared radiation source is a Xenon arc flashlamp.

4. An infrared gas detector as claimed in claim 1, wherein said first filter transmits a first wavelength band having a full width half maximum of 50±10 nm.

5. An infrared gas detector as claimed in claim 1, wherein said dual band pass second filter transmits a second wavelength band having a full width half maximum of 25±5 nm.

6. An infrared gas detector as claimed in claim 1, wherein said dual band pass second filter transmits a third wavelength band having a full width half maximum of 25±5 nm.

7. A method for monitoring for the presence of one or more of a plurality of target gases comprising volatile, potentially explosive $C_{1-7}$ alkane compounds using infrared radiation, the gases having differing absorption spectra, said method accurately indicating the concentration of such gases in service environments exhibiting differential attenuation of infrared radiation; said method comprising the steps of:

transmitting at least one beam of infrared radiation having a wavelength range that includes wavelengths of substantially 2215, 2300, and 2385 nm, the beam being transmitted along a beam path in which one or more target gases are received and which is subjected to a service environment;

forming a first wavelength band from the radiation traversing the beam path, said first wavelength band having a central wavelength of 2300±20 nm and a full width half maximum of 50±20 nm;

forming a second wavelength band from the radiation traversing the beam path, said second wavelength band having a central wavelength of 2215±20 nm and a full width half maximum of 25±20 nm;

forming a third wavelength band from the radiation traversing the beam path, said third wavelength band having a central wavelength of 2385±20 nm and a full width half maximum of 25±20 nm;

sensing the intensity of the radiation in said first wavelength band;

sensing the intensity of the radiation in said second and third wavelength bands; and indicating the presence of one or more target gases from the sensed intensities of the radiation in said first, second, and third wavelength bands.

8. A method as claimed in claim 7, wherein the step of forming the first wavelength band is further defined as forming a first wavelength band having a central wavelength of 2300±5 nm, and wherein the steps of forming the second and third wavelength bands are further defined as forming a second wavelength band having a central wavelength of 2215±5 nm and, a third wavelength band having a central wavelength of 2385±5 nm.

9. A method as claimed in claim 7, wherein the transmitting step is further defined as providing the infrared radiation by a Xenon arc flashlamp.

10. A method as claimed in claim 7, wherein the step of forming the first wavelength band is further defined as forming a first wavelength band having a full width maximum of 50±10 nm.

11. A method as claimed in claim 7, wherein the step of forming said second wavelength band is further defined as forming a second wavelength band having a full width half maximum of 25±5 nm.

12. A method as claimed in claim 7, wherein the step of forming said third wavelength band is further defined as forming a third wavelength band having a full width half maximum of 25±5 nm.

* * * * *